United States Patent [19]
Hori et al.

[11] Patent Number: 4,882,571
[45] Date of Patent: Nov. 21, 1989

[54] SENSOR USED FOR ELECTRICAL HEATING MEASUREMENT

[75] Inventors: Tomoshige Hori, Kitamoto; Yasuhiko Shiinoki, Tokyo; Kensuke Itoh, Kodaira, all of Japan

[73] Assignee: Snow Brand Milk Products Co., Ltd., Japan

[21] Appl. No.: 224,099

[22] Filed: Jul. 26, 1988

[30] Foreign Application Priority Data

Aug. 12, 1987 [JP] Japan ................... 62-201628

[51] Int. Cl.$^4$ ............................................. H01C 7/00
[52] U.S. Cl. ....................................................... 338/28
[58] Field of Search ..................... 338/14, 28, 30, 36; 324/65 P

[56] References Cited

U.S. PATENT DOCUMENTS

| 3,123,790 | 3/1964 | Tyler | 338/28 |
| 3,286,214 | 11/1966 | Kolb et al. | 338/28 X |
| 3,748,624 | 7/1973 | Yazawa et al. | 338/30 |
| 3,761,857 | 9/1973 | Carlson et al. | 338/30 |
| 4,178,544 | 12/1979 | Hoffman | 324/65 P X |

Primary Examiner—Donald A. Griffin
Attorney, Agent, or Firm—Griffin, Branigan & Butler

[57] ABSTRACT

A sensor used for electrical heating measurement comprises a sensor element having a rod, plural through holes provided straightly through the sensor in the longitudinal direction and plural metal thin wires inserted into and passed through the through holes and an electrically insulating member covering the sensor element, preferably the metal thin wires thinner than through holes are used, spaces around the metal thin wires are filled with ceramics powder and the powder is sintered by heating at lower temperature than the sintering temperature thereof.

11 Claims, 3 Drawing Sheets

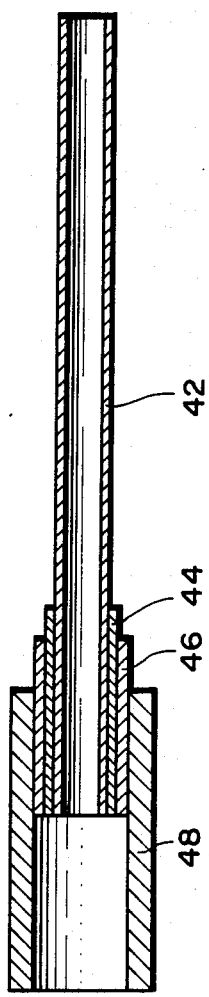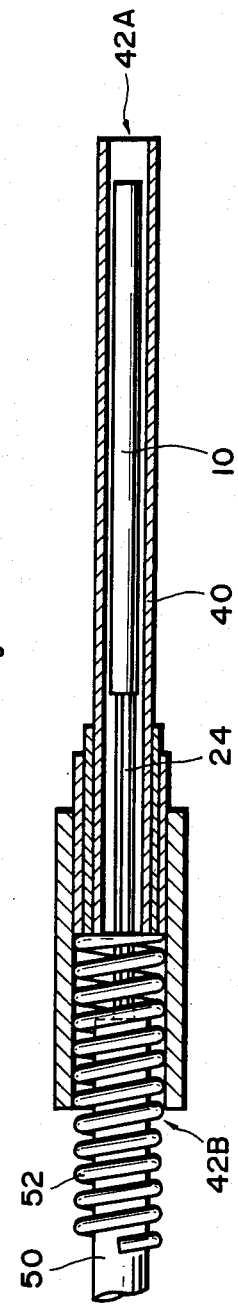

SENSOR USED FOR ELECTRICAL HEATING MEASUREMENT

BACKGROUND OF THE INVENTION

This invention relates to a sensor for measuring properties of many kinds of fluid by the socalled electrical heating measurement method.

The term "fluid" as used in the present specification means all kinds of fluid including a gaseous substance, a liquid substance or a solid substance such as powder or of two or more of these substances as well as a fluid of the type whose phase changes with time.

The inventors of this application have already proposed, in Japanese Patent Laid-open Application No. 62(1987)-56849, a sensor as follows.

A sensor for measurement by electrical heating has a core rod covered with an electrically insulating member, a thin metal wire wound about the core, and an electrically insulating member covering the thin metal wire.

In the above-mentioned traditional sensor, the thin metal wire is several times longer than the sensor since the thin metal wire is wound around the core rod. With this, the sensor has some advantageous such that the electric resistance increases according to the length of wire and therefore a large heat flux perunit length of the sensor can be obtained by a small electric current. Further, the sensor in itself is not easily cut, broken or bent.

On the other hand, since the thin metal wire is would around the core rod and spirally configured, a stress-strain occurs in the thin metal wire. And so there is a disadvantage such that, when an annealing treatment is performed in order to prevent the stressstrain thereof, the electric resistance thereof is largely changed from the initial value to some value which varies significantly with time.

the change of electric resistance of each sensor is different from other sensors and so it is difficult to determine the specific value common to each sensor.

Therefore, it is difficult to produce a sensor having a desirable electric resistance both before and after annealing. thus, the sensors are not interchangeable since each sensor has different electric resistance and so a relational equation between the electric resistance and properties of materials must be determined with each sensor.

SUMMARY OF THE INVENTION

Therefore, an object of the present invention is to provide a sensor having no stress-strain in the thin metal wire and where the electric resistance value is constant with time after an annealing treatment.

The object of the present invention can be attained by a sensor used for electrical heating measurement, comprising a sensor element having a rod, a plurality of holes (apertures) provided longitudinally through the sensor and a plurality of thin metal wires inserted into and through the through holes, and an electrically insulating member covering the sensor element.

According to the present invention, a stress-strain in a thin metal wire does not occur which is different from the traditional sensor formed by winding a thin metal wire around a core rod. Therefore, interchangeable sensors having a desired and predictable electric resistance value can be obtained. Further, in case of production on a large scale, each sensor will have a stable electric resistance value and so no adjustment for individual sensors is necessary.

Further, according to another aspect of the present invention, in addition to the above-mentioned technical means, there is provided a sensor for use in electrical heating measurement wherein the thin metal wires are thinner than the through holes and are inserted into and through the through holes. Spaced between the thin metal wires and the through holes is disposed a ceramic powder and the powder is sintered by heating at a temperature which is lower than the sintering temperature thereof.

In accordance with the second technical means, since in case of volumetric expansion with heating, the thin metal wire is not pressed against the inside of the holes in the rod, and the electric resistance of the sensor cannot be influenced by the stress-strain in the thin metal wire.

Furthermore, when two or more thin metal wires are inserted into holes in the rod in the longitudinal direction and are connected in series, the electric resistance of the wires increases to a corresponding extent, i.e. the same extent as the traditional sensor with wound wire, and a large heat flux per unit length of the sensor can be obtained by a small electric current.

BRIEF DESCRIPTION OF THE DRAWINGS

The above and other objects of the invention will be appreciated by reference to the description taken in connection with the accompanying drawings, in which:

FIG. 5 is a longitudinal section of a cover for the sensor, and FIG. 6 is an elevation view, partly in cross section, of a fully assembled sensor according to the present invention.

DESCRIPTION OF THE PREFERRED EMBODIMENT

Figure 1:
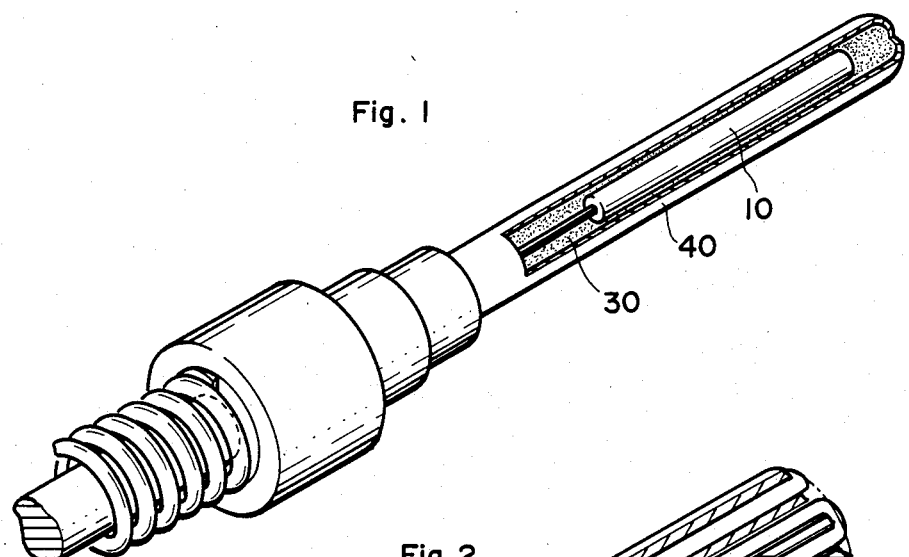
FIG. 1 is a perspective view, partly in cross section, of a sensor having a rod according to the present invention.

FIG. 1 shows a sensor according to the present invention, which is formed by covering a sensor element 10 with a cover 40.

Firstly, the sensor element 10 will be described hereinafter.

Figure 2:
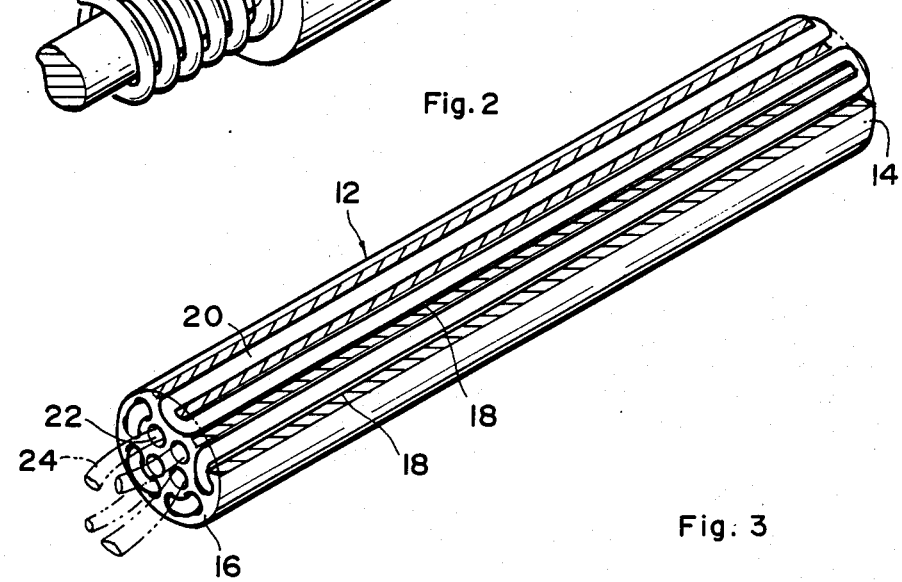
FIG. 2 is a perspective view, partly broken away, which shows the interior construction of the rod.
Figure 3:
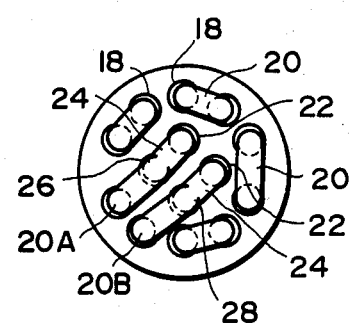
FIG. 3 is an end elevation view of the rod shown in FIG. 2.

A rod 12, as shown in FIG. 2, has ten through holes 18 for thin metal wires, which holdes pass entirely through the rod in the longitudinal direction and are equally spaced with respect to each other along the circumference of the rod. Further, four through holes 22 are provided adjacent to the center portion (axis) of the rod and inside the disposition of the through holes 18 for the thin metal wires. A plurality of straight thin metal wires 20 are inserted into and pass through the through holes 18.

The thin metal wires 20 are bent in a U-shape at the back end 16 and a pair of end portions of each thin metal wire is inserted into and pass through a pair of through holes 18 adjacent to each other from the back end surface 16 to the front end surface 14 of the rod 12. In the example in FIG. 2, five U-shape wires 20 are inserted into and pass through each pair of through holes 18 for the wires, and at the front end surface 14 an end portion of one wire is properly connected, e.g. by the spot welding, to an end portion of other wire adjacent to the above end portion. With this, wires 20 are connected in series and, thus, at the front end surface 14 only one resistance differential is formed between an end portion 20A and an end portion 20B.

On the other hand, two straight lead wires 24, 24 are inserted into and pass through the through holes 22 for lead wires 24. The lead wires 24 are also bent in U-shape in the same way as the above-mentioned method of the thin metal wire 20 and a pair of end portions of each lead wire are inserted into and pass through a pair of through holes 22 adjacent to each other, but, from the front end surface 14 to the back end surface 16 of the rod 12 which is opposite to the insertion of the thin metal wire 20. At the front end surface 14 the end portions 20A, 20B of the thin metal wires 20 are connected with contact points 26, 28 of the two lead wires 24, 24, e.g. by spot welding.

With this, the two lead wires 24, 24 are connected with the contact points 26 and 28 whereby the electric resistance of the thin metal wire 20 may be measured by the known four terminal method. For example, the thermal change of an atmosphere in which the sensor is disposed can be determined by connecting a current source and a voltmeter with the lead wires, adequately electrifying the thin metal wires 20, simultaneously measuring a voltage between the contact points 26 and 28 and calculating the electric resistance of the thin metal wires 20.

Figure 4:
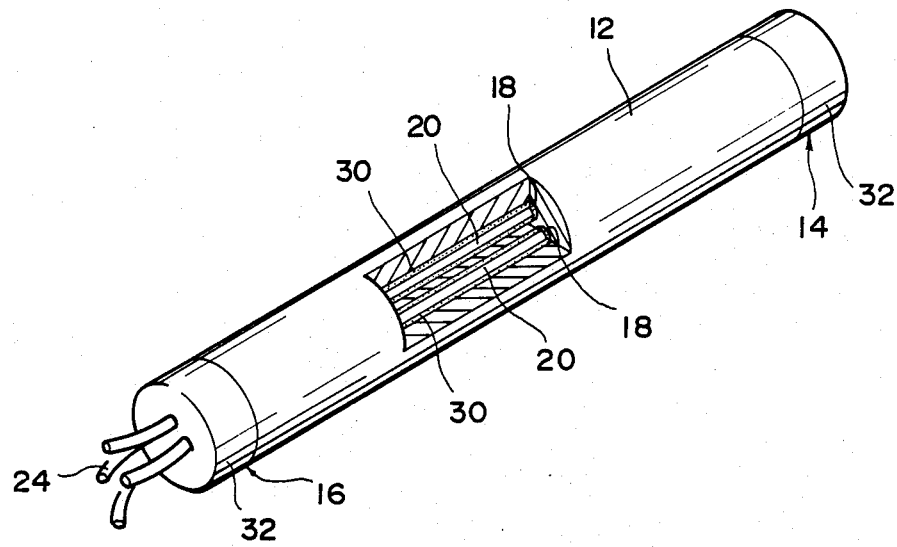
FIG. 4 is a perspective view, partly broken away, which shows the interior construction of the rod of sensor element.

As shown in FIG. 4, the thin metal wire 20 and the lead wire 24 are of slightly smaller diameter than that of the through holes 18 and the lead wire holes 22. Ceramics powder 30 are filled into the space in the through holes 18 and the lead wire holes 22. A glass sealing 32 is provided to both the front end surface 14 and the back end surface 16 of the rod 12 in order to prevent leakage of the ceramics powder 30.

The filled ceramics powder 30 is sintered at a low temperature. In this specification, the "low temperature" means a temperature lower than the sintering temperature of the ceramics.

With this, the ceramics powder 30 sintered at a low temperature can prevent an eccentricity of the thin metal wire 20. Further, when a volumetric expansion of the thin metal wire 20 occurs with heat, since the sintering state is easily destroyed, the thin metal wire 20 is not pressed against the inside of holes 18 and therefore no stress-strain occurs in the thin metal wire 20.

In the sensor element 10 of the above-mentioned example, the rod 12 is a column having a 1.4mm diameter and 100mm length and made of a ceramics having a high purity (more than 99.9%) of a sintered crystallized alumina. The thin metal wire 20 is a platinum wire having a 0.110mm diameter and the lead wire 22 is a platinum wire having a 0.15mm diameter. Holes 18 having a 0.16mm diameter are provided along the rod 12, and lead wire holes 22 having 0.16mm diameter are provided in the center of the rod 12.

The rod 12 of ceramics provides high workability and high strength and the rod, therefore, is not changed in quality or deformed. Further, the coefficient of volumetric expansion thereof is more or less the same as that of platinum. The thin metal wire 20 is made of platinum and provides stability of the electric resistance thereof.

The electric resistance of such a sensor is 10 Ω, the platinum wire having 0.110mm diameter is 10 Ω/m and therefore the desired value is determined according to these values. In case of a production on a large scale, the error of electric resistance of each sensor element 10 is about ±0.1% and the electric resistance has high stability both with time and with a heating-cooling procedure.

Further, the lead wire 24 is inserted into the center of rod 10 so that the lead wire 24 is not directly exposed to the temperature imposed on sensor element 10 in order to prevent a heat outflow from the lead wire 24. With this the heat of the thin metal wire 20 will not radiate out through the lead wire 24.

Next, a cover 40 covering the sensor element 10 will be described. As shown from FIG. 5, short pipes 44, 46 and a pipe 48 are provided to a back end portion of a pipe 42 having a slightly larger internal diameter than the sensor element 10.

These pipes are fixed uniformly by calking from the circumference thereof.

For example, stainless steel (SUS 316L), platinum, palladium and titanium are used as a pipe material; however, the pipe material is optionally determined in accordance with intended conditions.

After inserting the sensor element 10 into the pipe 42 adjacent to the front end thereof, a vacuum is applied from the front end of the pipe 42A and a resin is filled into the cover 40 from the back end 42B thereof for electrically insulating it from open air.

Ceramics powder, e.g. magnesium oxide powder and so on can be filled into the cover 40 in place of resin.

As described, the lead wire 24 can be connected to a cable 50 which is secured to cover 40 and a spring means 52 may be provided for protecting the cable 50 so as to obtain a sensor having excellent durability.

The cover 40 described above is only one example of that which may be used as an electrically insulating cover for the sensor element 10 and is not a limitation on the construction of the present sensor, with the exception that the cover must be an electrically insulating cover for the sensor element 10.

As clarified from the above description, the sensor according to the present invention can be applied for use as a resistance temperature sensor to measure the atmosphere in which the sensor is disposed by electrifying the thin metal wire, simultaneously measuring the voltage applied to the thin metal wire to obtain the change of the electric resistance.

As another application, two sensors according to the present invention are disposed in the fluid and one is used as a heat build-up element and another is used as a resistanct temperature sensor for measuring thermal conductivity so as to determine many of the properties of the fluid according to these values. Further, the present invention can be applied in any field as desired.

While there has been described what is at present considered to be preferred embodiment of the invention, it will be understood that various modifications may be made therein, and it is intended to cover in the appended claims all such modifications as fall within the true spirit and scope of the invention.

We claim:

1. In a sensor for determining physical properties of a fluid by electrically heating measurements in which an electrical current source and a voltmeter are connected to a plurality of thin metal wires associated with the sensor, the thin metal wires are heated by current from the current source and the voltage in the thin metal wires is measured while heat is transferred from the sensor to the fluid, the improvement comprising a sensor having:
- (A) an elongated rod;
- (B) a plurality of first holes disposed axially through said rod;
- (C) a plurality of thin metal wires disposed through said first holes; and
- (D) an electrically insulating member covering the sensor.

2. The sensor according to claim 1, wherein the plurality of thin metal wires are connected in series at an end portion of the rod.

3. The sensor according to claim 1, wherein the sensor is disposed in a cover larger than the sensor and the space between the sensor and the cover is filled with a resin.

4. The sensor according to claim 1, wherein the thin metal wires have a diameter smaller than the diameter of said holes, said wires are disposed ins aid holes, and the spaces between the said wires and the said holes are filled with ceramics powder, which powder is sintered by heating at a temperature which is lower than the sintering temperature of the said powder.

5. The sensor according to claim 4, wherein the said wires are connected in series at an end portion of the rod.

6. The sensor according to claim 8, wherein a plurality of lead wire holes are disposed through the rod, a plurality of lead wires are disposed in the lead wire holes and the lead wires are connected with the said thin metal wires at an end portion of the rod.

7. The sensor of claim 1 wherein there are a plurality of second holes disposed axially through said rod and a plurality of lead wires disposed through said second holes.

8. The sensor of claim 7 wherein the said first holes are disposed generally along the circumference of the rod.

9. The sensor of claim 8 wherein the said second holes are disposed adjacent the center portion of the rod.

10. The sensor of claim 9 wherein the said thin metal wires are connected in series, an the said lead wires are connected to the thin metal wires at one end thereof.

11. A sensor for use in electrical heating measurements, comprising:
- (A) a rod;
- (B) a plurality of holes disposed axially through said rod;
- (C) a plurality of U-shaped thin metal wires disposed through said holes from one end of the rod and the ends of said wires are connected in series with each other at the other end of the rod; and
- (D) an electrically insulated member covering the sensor.

* * * * *